United States Patent [19]

Miyahara et al.

[11] Patent Number: 5,434,411
[45] Date of Patent: Jul. 18, 1995

[54] INFRARED SPECTRUM MEASURING APPARATUS ADAPTED FOR MEASURING THE ABSORPTION OF INFRARED RADIATION BY A LIQUID SAMPLE UTILIZING A TOTAL REFLECTION PHENOMENON OF LIGHT

[75] Inventors: Yuji Miyahara, Hitachi; Toshiko Fujii; Yoshio Watanabe, both of Kokubunji, all of Japan

[73] Assignee: Hitachi, Ltd., Tokyo, Japan

[21] Appl. No.: 58,610

[22] Filed: May 6, 1993

[30] Foreign Application Priority Data

May 26, 1992 [JP] Japan ................................. 4-133370

[51] Int. Cl.⁶ ............................................. G01N 21/35
[52] U.S. Cl. ..................... 250/339.07; 250/339.08; 250/339.11; 250/339.12; 250/341.1; 250/341.8
[58] Field of Search ................... 250/339, 341

[56] References Cited

FOREIGN PATENT DOCUMENTS 4353747 12/1992 Japan .............................. 250/339.11

OTHER PUBLICATIONS

Hartstein et al., "Enhancement of the Infrared Absorption from Molecular Monolayers with Thin Metal Overlayers", Phys. Rev. Letters, 45(3), Jul. 21, 1980, pp. 201–204.

Applied Spectroscopy, 44, pp. 512–518, "FT–IR Metal Overlayer ATR Spectroscopy Using a Coated Elastomer Backing Material", C. G. L. Khoo and H. Ishida, 1990.

Primary Examiner—Carolyn E. Fields
Attorney, Agent, or Firm—Kenyon & Kenyon

[57] ABSTRACT

Infrared radiation is incident on a total reflection plane of a prism and penetrates a liquid sample through a metal layer put between the total reflection plane and the liquid sample in close contact therewith whereby the infrared radiation is partially absorbed by the liquid sample. Alternatively, the liquid sample may be put between the total reflection plane and the metal layer in close contact therewith so that part of the light penetrates the sample from the prism through the total reflection plane to interact with the metal layer and then is caused to reenter into the prism whereby it is partly absorbed by the liquid sample. The metal layer is for enhancing the intensity of the electric field component of the infrared radiation. The incident angle of the infrared radiation on the total reflection plane is so set that the partially absorbed infrared radiation is total-reflected. The total-reflected infrared radiation is detected by a detector so as to obtain an absorption spectrum of the liquid sample by the infrared radiation.

17 Claims, 4 Drawing Sheets

INFRARED SPECTRUM MEASURING APPARATUS ADAPTED FOR MEASURING THE ABSORPTION OF INFRARED RADIATION BY A LIQUID SAMPLE UTILIZING A TOTAL REFLECTION PHENOMENON OF LIGHT

BACKGROUND OF THE INVENTION (1) Field of the Invention

The present invention relates to an infrared spectrum measuring apparatus, and more particularly to an infrared spectrum measuring apparatus adapted for measuring the absorption of infrared radiation by a liquid sample utilizing a total reflection phenomenon of light.

(2) Description of the Prior Art

Regarding conventional infrared spectroscopic analysis, a report dealing with the increasing of the infrared absorption of a sample by enhancing the intensity of an electric field component of infrared radiation using a metal provided on an attenuated total reflection has been described in Applied Spectroscopy 44 (1990), pp 512–518. In this paper, it is discussed that when a sample layer of molecules with high molecular weight is mounted on an attenuated total reflection prism and further a metal layer formed on an elastic membrane is provided via an air gap, the infrared absorption by the sample is increased by a sandwich effect due to a difference in refractive indices.

Because sensitivity in the foregoing conventional art depends greatly on the thicknesses of the sample and the air gap, unless the thicknesses of the sample and air gap are precisely controlled with a precision of some several nm, infrared absorption spectra cannot be obtained with a better reproducibility, thereby it is difficult to carry out any quantitative analyses without taking some effective measures to solve such problems. Further, hereinabove only a sample layer of molecules with high molecular weight is addressed and measurement of any liquid sample is not taken into account.

SUMMARY OF THE INVENTION

An object of the present invention is to provide an infrared spectrum measuring apparatus adapted to measure the absorption of infrared radiation by a liquid sample with high sensitivity utilizing a total reflection phenomenon of light.

Another object of the present invention is to provide an infrared spectrum measuring apparatus adapted to measure the absorption of infrared radiation by a liquid sample with improved reproducibility utilizing a total reflection phenomenon of light.

According to an aspect of the present invention, an infrared spectrum measuring apparatus is provided which comprises an infrared radiation transmitting medium having a total reflection plane; means for generating infrared radiation and directing the same from the outside of the infrared transmitting medium to the inside thereof so as to cause the infrared radiation to be incident on the total reflection plane; a layer disposed so as to come in close contact with the total reflection plane on one side thereof and a liquid sample on the other side, respectively, the layer having its thickness capable of transmitting the infrared radiation therethrough and of causing the same to penetrate the liquid sample so that the infrared radiation is partially absorbed thereby, the layer being for enhancing the intensity of an electric field component of the infrared radiation, and the incident angle of the infrared radiation on the total reflection plane being so set that the partially absorbed infrared radiation is substantially total-reflected; and means for detecting the total-reflected infrared radiation.

According to another aspect of the present invention, an infrared spectrum measuring apparatus is provided which comprises an infrared radiation transmitting medium having a total reflection plane; means for generating infrared radiation and directing the same from the outside of the infrared transmitting medium to the inside there of so as to cause the infrared radiation to be incident on the total reflection plane; a metal layer disposed so as to come in close contact with the total reflection plane on one side thereof and a liquid sample on the other side, respectively, the metal layer having its thickness capable of transmitting the infrared radiation therethrough and of causing the same to penetrate the liquid sample so that the infrared radiation is partially absorbed thereby, and the incident angle of the infrared radiation on the total reflection plane being so set that the partially absorbed infrared radiation is substantially total-reflected; and means for detecting the total-reflected inflared.

According to still another aspect of the present invention, an infrared spectrum measuring apparatus is provided which comprises an infrared radiation transmitting medium having a total reflection plane; means for generating infrared radiation and directing the same from the outside of the infrared radiation transmitting medium to the inside thereof so as to cause the infrared radiation to be incident on the total reflection plane; a metal layer disposed apart from the total reflection plane so as to form a layer-like space between the total reflection plane and the metal layer, the layer-like space being filled with a liquid sample so as to bring the same into close contact with the total reflection plane and the metal layer, the thickness of the layer-like space being so set that the infrared radiation is transmitted therethrough and partially absorbed by the liquid sample, and the incident angle of the infrared radiation on the total reflection plane being so set that the partially absorbed infrared radiation is substantially total-reflected; and means for detecting the total-reflected infrared radiation.

Other objects, features and advantages of the present invention will become apparent from the description of preferred embodiments of the present invention in conjunction with the accompanying drawings.

DESCRIPTION OF THE PREFERRED EMBODIMENTS

Figure 1:
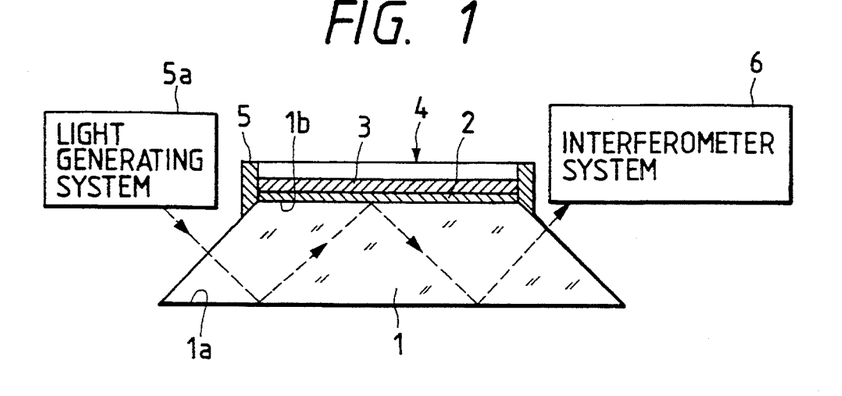
FIG. 1 is a conceptual view, partly in section, of the main portion of an infrared spectrum measuring apparatus showing an embodiment according to the present inventions.

Referring to FIG. 1, a trapezoidal prism 1 is provided with a reflection plane 1a and a total reflection plane 1b parallel thereto, and is made of, for example, KRS-5, KRS-6, ZnSe, Ge, Si, AgCl or AgBr so as to be capable of transmitting infrared radiation therethrough. Formed or disposed on the total reflection plane 1b of the prism 1 in close contact therewith by vacuum deposition, electron beam deposition, sputtering or the like is a metal film or layer 2, which may be made of silver, gold, platinum, alminum, nickel, palladium or a mixture thereof, or may be a lamination of such metals. A liquid sample 3 is accommodated in a sample container 4, which is constituted by the metal layer 2 and a side member 5 secured to the prism 1 in a liquid-proof manner to thereby bring the liquid sample into close contact with the opposite surface of the metal layer 2 to the prism 1.

Infrared radiation generated by a light generating system 5a is directed from the outside of the prism 1 to the inside thereof so as to be incident on the total reflection plane 1b after reflected by the reflection plane 1a. The metal layer 2 has its thickness capable of transmitting the infrared radiation therethrough and of causing the same to penetrate the liquid sample 3 so that the infrared radiation is partially absorbed thereby. The incident angle of the infrared radiation on the total reflection plane 1b is so set that the partially absorbed infrared radiation is total-reflected. The total-reflected infrared radiation, after reflected by the reflection plane 1a, is conducted to an interferometer system 6 arranged outside of the prism 1. In the interferometer system, the infrared radiation is divided into two light beams in order to introduce these light beams into an interferometer for light interference with each other. Then, the two light beams are converted into a composite light beam thereof, the composite light beam being detected by a light detector to be thereby converted into an electric signal. When the optical path difference between the two light beams is varied, the electric signal is representative of a function of the optical path difference, thus getting an interferogram. If the interferogram is Fourier-transformed, then an infrared absorption spectrum of the liquid sample is obtained.

The interferometer of the interferometer system 6 may be arranged between the light generating system 5a and the prism 1, because, even in the case of such an arrangement, the same results as in the foregoing can be expected.

When the infrared radiation is transmitted through the metal layer 2, the intensity of an electric field component of the infrared radiation is enhanced because of their interaction. In addition, the thickness of the metal layer can be controlled with high precision. Thus, the infrared absorption spectrum is measured with high sensitivity and with high reproducibility.

Figure 2:
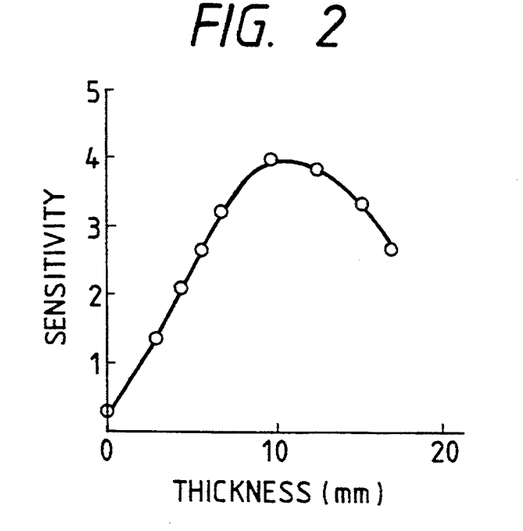
FIG. 2 is a graph showing the effect of the thickness of a silver-made layer on a detection sensitivity characteristic according to the embodiment shown in FIG. 1.

FIG. 2 shows the effect of the thickness of a metal layer 2 made of silver on a detection sensitivity characteristic, which represents a plot of measured absorption spectral peak values at a wave number of 1030 cm$^{-1}$ of glucose based on pyranose rings in a glucose solution. As obvious from FIG. 2, the detection sensitivity increases with an increasing thickness of the silver layer, becoming the maximum at about 10 nm of thickness. Thus, it is preferable for a thickness of the silver layer to be set approximately at 10 nm. As stated already, the metal layer 2 may be made of other metals. In such a case, its thickness may vary depending on a kind, a combination or the like, but it is preferable to be less 100 nm.

In general, a metal layer formed on a surface by deposition is composed of a number of island-like layer elements which are distributed in close proximity to one another and each comprises a group of metal particles. Such a metal layer may be preferably utilized for the metal layer 2.

Figure 3:
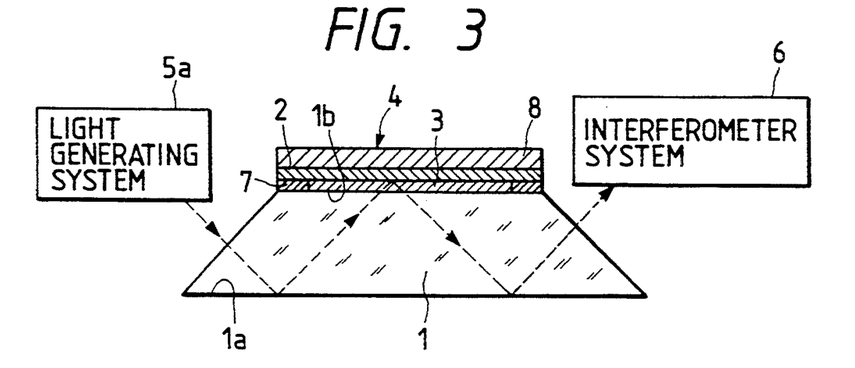
FIG. 3 is a conceptual view, partly in section, of the main portion of an infrared spectrum measuring apparatus showing another embodiment according to the present invention.

Referring to FIG. 3, a spacer 7 is formed on the total reflection plane 1b of the prism 1, then via this spacer 7 there is mounted a plate 8 supporting the metal layer 2 formed on one side thereof. The metal layer 2 is disposed to face the total reflection plane 1b of the prism 1. By means of the spacer 7, a layer-like space is retained between the plane 1b of the prism 1 and the plate 8, into which the liquid sample 3 is introduced utilizing the capillary phenomenon or action, for example. The liquid sample 3 intervening between the plane 1b of the prism 1 and the metal layer 2 is in close contact therewith, the thickness of which is thus dependent on that of the spacer 7.

The thickness of the spacer 7 is smaller (shallower) than a permeation or penetration depth of the infrared radiation and consequently, part of the light penetrating the sample 3 from the prism 1 through the total reflection plane 1b interacts with the metal layer 2 and then is caused to reenter (reflect) into the prism 1.

When zinc selenide is used for the prism, and when an incident angle is set at 45 degrees, a penetration depth of the infrared radiation becomes approximately 2 $\mu$m, thereby the spacing between the metal layer 2 and the prism 1 must be set at a thickness less than 2 $\mu$m.

According to this embodiment of the invention, since the optical path length in the sample is capable of being controlled precisely by controlling the thickness of the spacer 7, a good reproducibility is ensured. Further, since part of the light is caused to reenter the sample 3 with the electrical field component thereof being enhanced as the result of interaction with the metal layer 2, it is possible obtain high sensitivity infrared absorption spectra. Further, the plate 8 may be a metal plate itself.

Figure 4:
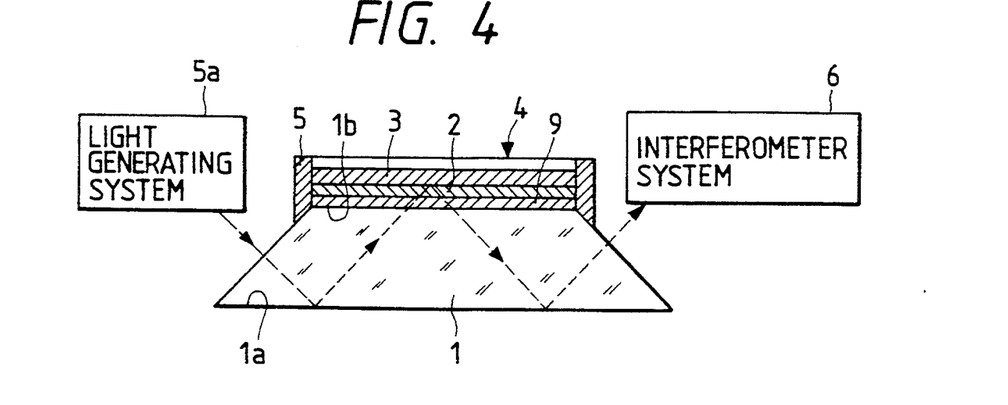
FIG. 4 is a conceptual view, partly in section, of the main portion of an infrared spectrum measuring apparatus showing an additional embodiment according to the present invention.

Referring to FIG. 4, an embodiment shown in this FIG. 4 differs from that shown in FIG. 1 in that an organic film or layer 9 is put between the total reflection plane 1b of the prism 1 and the metal layer 2 in close contact therewith.

The organic layer 9 is formed of one of polyvinyl chloride, cellulose, polyurethane and silicone, or the same comprises such molecules that can be polymerized by ultraviolet, electron beams, radiations, which include vinyl compounds such as stearatevinyl and octadecyl acrylate, or diacetylene compounds, diene compounds and the like, the layer thickness of which, in either case, is controlled to within, at least, 1/5 of the wavelength of the infrared radiation to use.

Each thickness of the organic layer 9 and the metal layer 2 is set at 10 nm or less, and a total thickness of the organic layer 9 and the metal layer 2 is made thin enough to allow the infrared radiation to penetrate the liquid sample 3.

According to the embodiment in FIG. 4, part of light 4 in the prism 1 is allowed to transmit through the organic layer 9 and the metal layer 2 while interacting with the metal layer 2 into the sample, thereby a high sensitivity spectrum is obtained.

Further, since the organic layer 9 is formed on the prism 1, adsorption of proteins, for instance, in the liquid sample onto the prism can be minimized, thereby reproducibility in the repeated use of specimens can be improved substantially.

Figure 5:
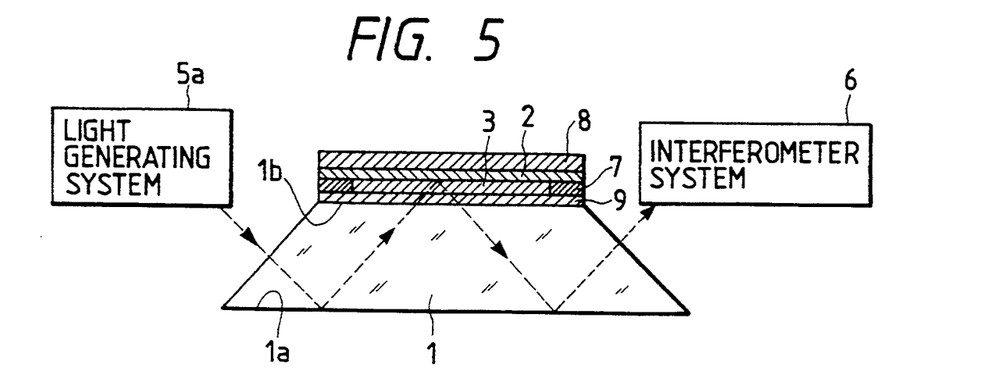
FIG. 5 is a conceptual view, partly in section, of the main portion of an infrared spectrum measuring apparatus showing a yet another embodiment according to the present invention.

Referring to FIG. 5, an embodiment shown in this FIG. 5 is similar to that of FIG. 3, but differs from the same in that the organic film or layer 9 is inserted between the total reflection plane 1b of the prism 1 and the spacer 7 in close contact with the total reflection plane 1b of the prism 1 and the liquid sample 3 in the layer-like space.

According to this embodiment of the invention, a high sensitivity spectrum is obtained with an improved reproducibility as in the case of the embodiment shown in FIG. 3. In addition, because of the presence of the organic layer 9, the sample is prevented from direct contacting the prism 1. Therefore, any disturbance due to adsorption, for example, of protein can be minimized, thereby improving the reproducibility for the repeated use of specimens.

Figure 6:
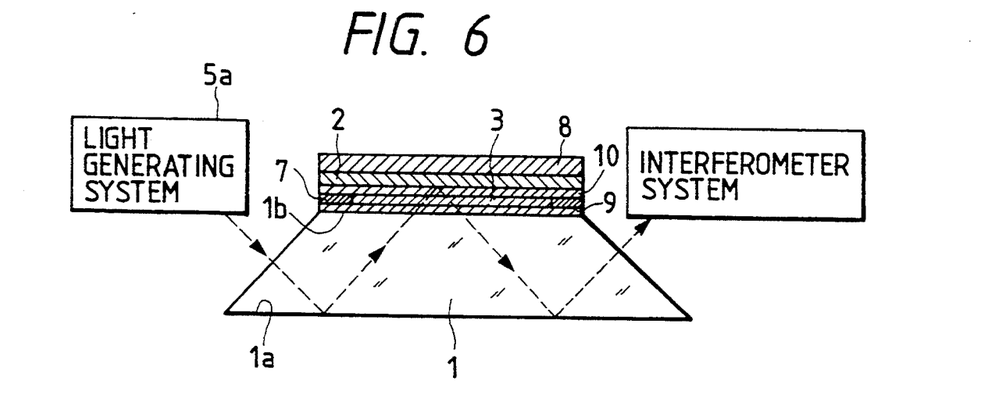
FIG. 6 is a conceptual view, partly in section, of the main portion of an infrared spectrum measuring apparatus showing a further embodiment according to the present invention.

Referring to FIG. 6, an embodiment shown in this FIG. 6 is similar to that of FIG. 5, but is different in that an intermediate layer 10 is put between the spacer 7 and the metal layer 2 in close contact with the liquid sample 3 in the layer-like space and the metal layer 2.

The intermediate layer 10 is made of an organic or inorganic material having a refractive index of 1.5 or less such as a high molecular compound, glass, silicon oxide which has a least absorption in the infrared wavelength range to use. Since the intermediate layer 10 is a solid, the precise thickness control thereof is possible. The intermediate layer 10 serves also to prevent possible protein in the liquid sample 3 from being adsorbed by the metal layer 2.

Further, since the thickness of the liquid sample 3 can be controlled precisely by means of the spacer 7, it is possible to obtain a high sensitivity spectrum with a better reproducibility.

Figure 7:
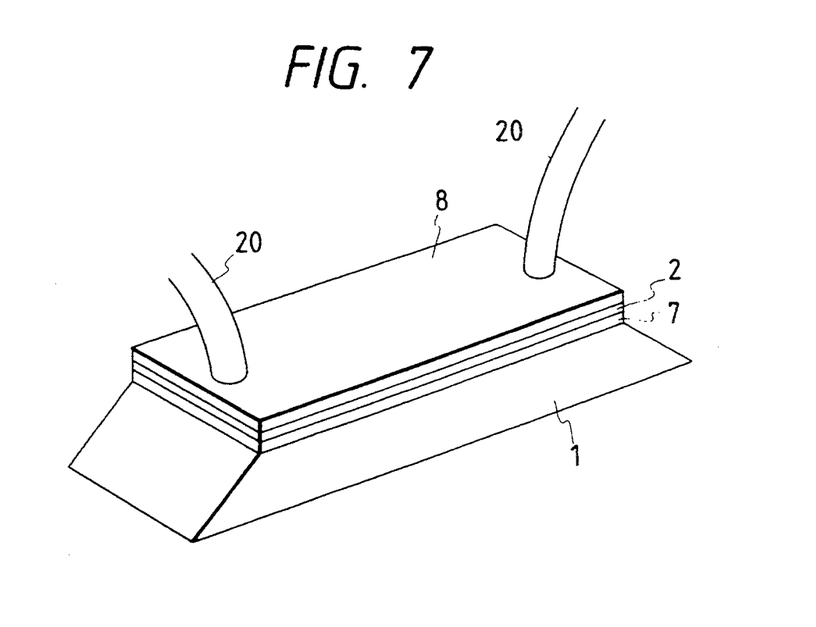
FIG. 7 is a conceptual perspective view of the main portion of an infrared spectrum measuring apparatus showing a further additional embodiment according to the present invention.

Referring to FIG. 7, an embodiment shown in this FIG. 7 represents a modification of the embodiments shown in FIGS. 3, 5 and 6, wherein tubes 20 are provided for use in introducing and discharging the liquid sample 3 into and out of the layer-like space to thereby utilize it as a flow cell space.

According to this embodiment, the liquid sample 3 can be repeatedly introduce and discharged into and out of the layer-like space by means of a pump or the like.

Figure 8:
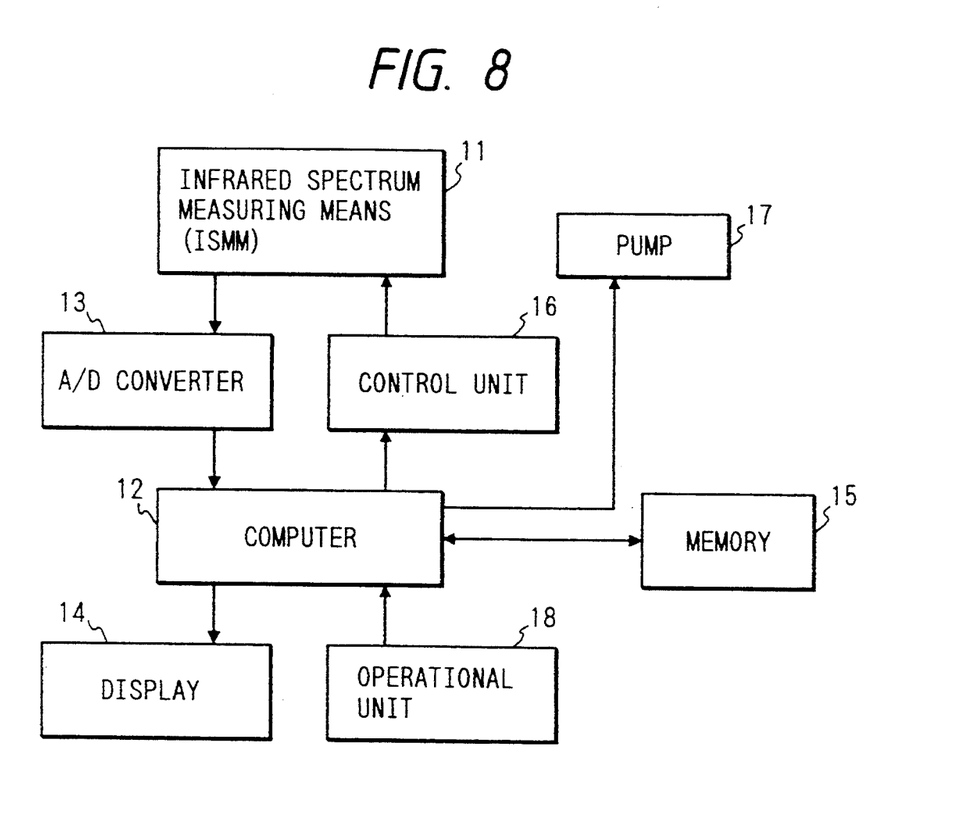
FIG. 8 is a schematic block diagram of an infrared spectrum measuring apparatus showing an embodiment according to the present invention.

Referring to FIG. 8, numeral 11 designates the entire system as shown in FIGS. 1, 3, 4, 5 or 6, which is hereinafter called "an infrared spectrum measuring means (ISMM)".

An output signal representative of an interferogram from the ISMM is introduced into a computer 12 through an A/D converter 13 so as to Fourier-transform the output signal to thereby convert the same into an infrared absorption spectrum. The computer 13 further executes data processing such as calculation of the absorption spectrum peak area and conversion of the same into a concentration for displaying the results of concentration calculation and other necessary information on a display 14. In addition, the computer 13 is provided with a memory 15 connected thereto, and therefore the results of computation on the spectrum, concentrations and the like can be stored therein.

A control unit 16 controls the interferometer to thereby scan the optical path difference thereof in response to a control signal from the computer 13.

In the case where the embodiment of FIG. 7 is adopted, a liquid sample feeding pump 17 can be added thereto. Analytical operation can be executed readily by the operator who is required only to entry necessary information via an operational unit 18, and thus it is possible to provide an easy-to-use analytical apparatus.

Figure 9:
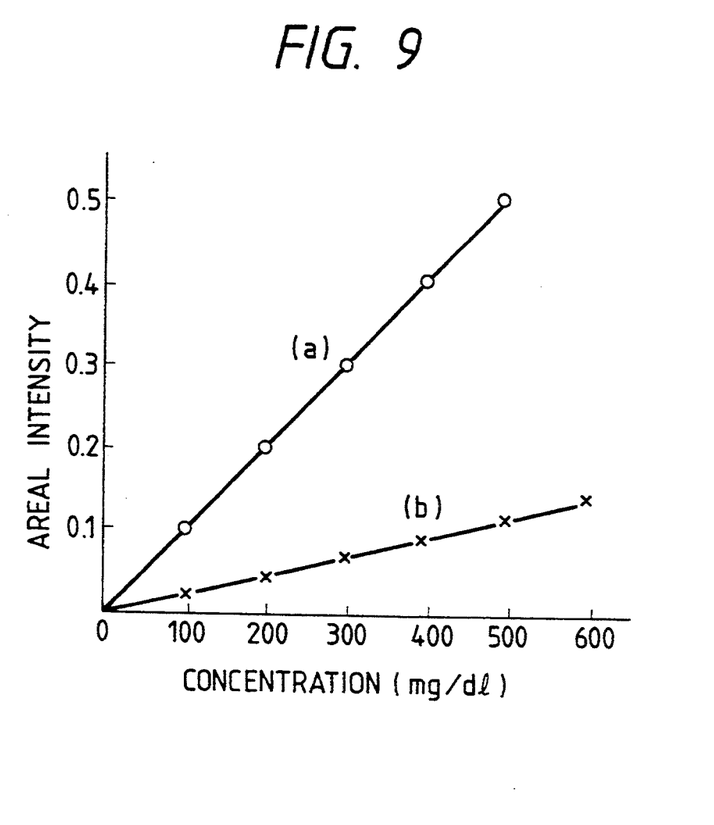
FIG. 9 is a graph showing calibration curves obtained by measuring infrared absorption spectra of a glucose sample solution.

FIG. 9 shows calibration curves obtained by plotting infrared absorption spectra of a glucose solution as measured utilizing the embodiment of FIG. 8. In FIG. 8, the coordinate represents the areal intensity of the spectrum in the wave number range from 1180 cm$^{-1}$ to 950 cm$^{-1}$ and the abscissa represents the concentration of glucose. The data (a) was obtained when the embodiment of FIG. 1 was adapted wherein the metal layer 2 was made of silver and a thickness thereof was set at 10 nm, while the data (b) was obtained when not adopted. It is clearly understood that according to the embodiment can be carried out with high sensitivity.

According to the embodiments of the present invention, as seen from the foregoing, the absorption measurement or analysis of a liquid sample by infrared radiation can be carried out with high sensitivity and with high reproducibility. Further, by mounting an organic film on the reflection plane of the prism according to the invention, in particular, in the case where the liquid specimen contains proteins or the like, adsorption of protein substances of the attenuated total reflection prism can be minimized, thereby reproducibility even in repeated replacements of specimens can be improved.

Since it is obvious that many changes and modifications can be made in the above described details without departing from the nature and spirit of the invention, it is to be understood that the invention is not to be limited to the details described herein except as set forth in the appended claims.

What is claimed is:

1. An infrared spectrum measuring apparatus comprising:
   a) a prism having a total reflection plane;
   b) means for generating infrared radiation and directing the same from the outside of the prism to the inside thereof so as to cause the infrared radiation to be incident on the total reflection plane, wherein the prism has another reflection plane substantially parallel to the total reflection plane so that the infrared radiation is reflected a plurality of times between these reflection planes;
   c) a layer disposed so as to come in close contact with the total reflection plane;

d) a sample container comprising means for accommodating a liquid sample, said sample container comprising side walls and said layer,
  (i) the layer having its thickness capable of transmitting the infrared radiation therethrough and of causing the same to penetrate the liquid sample so that the infrared radiation is partially absorbed thereby,
  (ii) the layer being for enhancing the intensity of an electric field component of the infrared radiation, and
  (iii) the incident angle of the infrared radiation on the total reflection plane being so set that the partially absorbed infrared radiation is substantially total-reflected; and
e) means for detecting the total-reflected infrared radiation, wherein the electric field component intensity enhancing layer comprises a metal layer and an organic layer disposed between the prism and the metal layer to come in close contact with them, the organic layer being capable of transmitting the infrared radiation therethrough.

2. The infrared spectrum measuring apparatus according to claim 1, wherein the thickness of the organic layer is substantially less than 1/5 of the wavelength of the infrared radiation.

3. An infrared spectrum measuring apparatus comprising:
a) a prism having a total reflection plane;
b) means for generating infrared radiation and directing the same from the outside of the prism to the inside thereof so as to cause the infrared radiation to be incident on the total reflection plane, wherein the prism has another reflection plane substantially parallel to the total reflection plane so that the infrared radiation is reflected a plurality of times between these reflection planes;
c) a metal-containing layer disposed so as to come in close contact with the total reflection plane;
d) a sample container comprising means for accommodating a liquid sample, said sample container comprising side walls and said metal-containing layer,
  (i) the metal-containing layer having its thickness capable of transmitting the infrared radiation therethrough and of causing the same to penetrate the liquid sample so that the infrared radiation is partially absorbed thereby, and
  (ii) the incident angle of the infrared radiation on the total reflection plane being so set that the partially absorbed infrared radiation is substantially total-reflected; and
e) means for detecting the total-reflected infrared radiation, wherein the metal-containing layer comprises a metal layer and an organic layer, said organic layer being disposed between the prism and the metal layer to come in close contact with them, the organic layer being capable of transmitting the infrared radiation therethrough.

4. The infrared spectrum measuring apparatus according to claim 3, wherein the thickness of the organic layer is substantially less than 1/5 of the wavelength of the infrared radiation.

5. An infrared spectrum measuring apparatus comprising:
a) an infrared radiation transmitting medium having a total reflection plane;
b) means for generating infrared radiation and directing the same from the outside of the infrared radiation transmitting medium to the inside thereof so as to cause the infrared radiation to be incident on the total reflection plane;
c) a metal layer;
d) a spacer disposed between the total reflection plane and the metal layer for forming therebetween a layer-like space comprising means for holding a liquid sample and bringing the same into close contact with the total reflection plane and the metal layer,
  (i) the thickness of the spacer being so set that the infrared radiation is transmitted through the liquid sample and partially absorbed by the same, and
  (ii) the incident angle of the infrared radiation on the total reflection plane being so set that the partially absorbed infrared radiation is substantially total-reflected; and
e) means for detecting the total-reflected infrared radiation.

6. The infrared spectrum measuring apparatus according to claim 5, further comprising a plate for supporting the metal layer.

7. An infrared spectrum measuring apparatus comprising:
a) an infrared radiation transmitting medium having a total reflection plane;
b) means for generating infrared radiation and directing the same from the outside of the infrared radiation transmitting medium to the inside thereof so as to cause the infrared radiation to be incident on the total reflection plane;
c) a metal-containing layer;
d) an organic layer being capable of transmitting the infrared radiation therethrough;
d) a spacer disposed between the organic layer and the metal-containing layer for forming therebetween a layer-like space comprising means for holding a liquid sample and bringing the same into close contact with the organic layer and the metal-containing layer,
  (i) the thickness of the spacer being so set that the infrared radiation is transmitted through the liquid sample and partially absorbed by the same, and
  ii) the incident angle of the infrared radiation on the total reflection plane being so set that the partially absorbed infrared radiation is substantially total-reflected; and
e) means for detecting the total-reflected infrared radiation.

8. The infrared spectrum measuring apparatus according to claim 7, wherein said metal-containing layer comprises a metal layer and a protection solid layer, said protection solid layer disposed between the layer-like space and the metal layer, the protection solid layer being in close contact with the metal layer on one side thereof and the liquid sample when the liquid sample fills the layer-like space on the other side, respectively.

9. The infrared spectrum measuring apparatus according to claim 8, wherein the thickness of the organic layer is substantially less than 1/5 of the wavelength of the infrared radiation.

10. An infrared spectrum measuring apparatus comprising:

a) an infrared radiation transmitting prism having a total reflection plane and another reflection plane substantially parallel thereto;
b) means for generating infrared radiation and directing the same from the outside of the infrared radiation transmitting prism to the inside thereof so as to cause the infrared radiation to be incident on the total reflection plane and be reflected a plurality of times between the two reflection planes;
c) an organic layer disposed so as to come in close contact with the total reflection plane, the organic layer being capable of transmitting the infrared radiation therethrough;
d) a metal layer disposed so as to come in close contact with the organic layer on the opposite side thereof to the total reflection plane;
e) a sample container comprising means for accommodating a liquid sample, said sample container comprising side walls and said metal layer,
  (i) the metal layer having its thickness capable of transmitting the infrared radiation therethrough and of causing the same to penetrate the liquid sample so that the infrared radiation is partially absorbed thereby,
  (ii) the metal layer being for enhancing the intensity of an electric field component of the infrared radiation, and
  (iii) the incident angle of the infrared radiation on the total reflection plane being so set that the partially absorbed infrared radiation is substantially total-reflected; and
f) means for detecting the total-reflected infrared radiation.

11. The infrared spectrum measuring apparatus according to claim 10, wherein the thickness of the organic layer is substantially less than 1/5 of the wavelength of the infrared radiation.

12. An infrared spectrum measuring apparatus comprising:
a) an infrared radiation transmitting prism having a total reflection plane and another reflection plane substantially parallel thereto;
b) means for generating infrared radiation and directing the same from the outside of the infrared radiation transmitting prism to the inside thereof so as to cause the infrared radiation to be incident on the total reflection plane and be reflected a plurality of times between the two reflection planes;
c) an organic layer disposed so as to come in close contact with the total reflection plane, the organic layer being capable of transmitting the infrared radiation therethrough;
d) a metal layer disposed so as to come in close contact with the organic layer on the opposite side thereof to the total reflection plane;
e) a sample container comprising means for accommodating a liquid sample, said sample container comprising side walls and said metal layer,
  (i) the metal layer having its thickness capable of transmitting the infrared radiation therethrough and of causing the same to penetrate the liquid sample so that the infrared radiation is partially absorbed thereby, and
  (ii) the incident angle of the infrared radiation on the total reflection plane being so set that the partially absorbed infrared radiation is substantially total-reflected; and
f) means for detecting the total-reflected infrared radiation.

13. The infrared spectrum measuring apparatus according to claim 12, wherein the thickness of the organic layer is substantially less than 1/5 of the wavelength of the infrared radiation.

14. An infrared spectrum measuring apparatus comprising:
a) an infrared radiation transmitting medium having a total reflection plane;
b) means for generating infrared radiation and directing the same from the outside of the infrared radiation transmitting medium to the inside thereof so as to cause the infrared radiation to be incident on the total reflection plane;
c) a metal layer;
d) a spacer disposed between the metal layer and the total reflection plane for forming therebetween a layer-like space comprising means for holding a liquid sample and bringing the same into close contact with the total reflection plane and the metal layer,
  (i) the thickness of the spacer being so set that the infrared radiation is transmitted through the liquid sample and partially absorbed by the same, and
  (ii) the incident angle of the infrared radiation on the total reflection plane being so set that the partially absorbed infrared radiation is substantially total-reflected;
e) a plate disposed so as to come in close contact with the metal layer on the opposite side thereof to the spacer for supporting the metal layer; and
f) means for detecting the total-reflected infrared radiation.

15. An infrared spectrum measuring apparatus comprising:
a) an infrared radiation transmitting medium having a total reflection plane;
b) means for generating infrared radiation and directing the same from the outside of the infrared radiation transmitting medium to the inside thereof so as to cause the infrared radiation to be incident on the total reflection plane;
c) an organic layer disposed so as to come in close contact with the total reflection plane;
d) a metal layer;
e) a spacer disposed between the organic layer and the metal layer for forming therebetween a layer-like space comprising means for holding a liquid sample and bringing the same into close contact with the organic layer and the metal layer,
  (i) the thickness of the spacer being so set that the infrared radiation is transmitted through the liquid sample and partially absorbed by the same, and
  (ii) the incident angle of the infrared radiation on the total reflection plane being so set that the partially absorbed infrared radiation is substantially total-reflected; and
f) means for detecting the total-reflected infrared radiation.

16. An infrared spectrum measuring apparatus comprising:
a) an infrared radiation transmitting medium having a total reflection plane;
b) means for generating infrared radiation and directing the same from the outside of the infrared radiation transmitting medium to the inside thereof so as to cause the infrared radiation to be incident on the total reflection plane;

c) an organic layer disposed so as to come in close contact with the total reflection plane;

d) a protection solid layer;

e) a spacer disposed between the organic layer and the protection solid layer for forming therebetween a layer-like space comprising means for holding a liquid sample and bringing the same into close contact with the organic layer and the protection solid layer, f) a metal layer disposed so as to come in close contact with the protection solid layer on the opposite side thereof to the spacer, (i) the thickness of the spacer being so set that the infrared radiation is transmitted through the liquid sample and partially absorbed by the same, and (ii) the incident angle of the infrared radiation on the total reflection plane being so set that the partially absorbed infrared radiation is substantially total-reflected; and g) means for detecting the total-reflected infrared radiation.

17. The infrared spectrum measuring apparatus according to claim 16, wherein the thickness of the organic layer is substantially less than 1/5 of the wavelength of the infrared radiation.

* * * * *

UNITED STATES PATENT AND TRADEMARK OFFICE
CERTIFICATE OF CORRECTION

PATENT NO. : 5,434,411
DATED : 18 July 1995
INVENTOR(S) : Yuji MIYAHARA et al.

It is certified that error appears in the above-identified patent and that said Letters Patent is hereby corrected as shown below:

| Column | Line | |
|---|---|---|
| 2 | 10 | Change "there of" to --thereof--. |
| 2 | 23 | Change "inflared" to --infrared--. |
| 2 | 50 | Change "DRAWING" to --DRAWINGS--. |
| 2 | 55 | Change "inventions" to --invention--. |
| 3 | 1 | Before "yet" delete "a". |
| 3 | 41 | Before "reflected" insert --it is--. |
| 3 | 49 | Before "reflected" insert --it is--. |
| 3 | 51 | After "system" insert --6--. |
| 3 | 61 | Change "getting" to --creating--. |
| 4 | 13 | After "As" insert --is--. |
| 4 | 19 | Change "a kind" to --the type of metal--. |

UNITED STATES PATENT AND TRADEMARK OFFICE
CERTIFICATE OF CORRECTION

PATENT NO.  : 5,434,411
DATED       : 18 July 1995
INVENTOR(S) : Yuji MIYAHARA et al.

It is certified that error appears in the above-identified patent and that said Letters Patent is hereby corrected as shown below:

| Column | Line | |
|---|---|---|
| 4 | 43 | After "and" insert --,--. |
| 5 | 7  | Before "use" insert --be--. |
| 5 | 35 | Change "direct" to --directly--. |
| 5 | 47 | Change "compound, glass, silicon" to --compound, like glass or silicon--. |
| 5 | 48 | After "oxide" insert --,--. |
| 5 | 49 | Change "use" to --be used--. |
| 5 | 65 | Change "introduce" to --introduced--. |
| 6 | 35 | Change "adopted" to --adapted--. |
| 6 | 36 | Before "can be" insert --that this measurement--. |

Signed and Sealed this

Twenty-third Day of January, 1996

Attest:

BRUCE LEHMAN

*Attesting Officer*      *Commissioner of Patents and Trademarks*